US010966799B1

(12) United States Patent
Cohen et al.

(10) Patent No.: US 10,966,799 B1
(45) Date of Patent: Apr. 6, 2021

(54) STABLE AFFIXATION SYSTEM FOR GUIDED DENTAL IMPLANTATION

(71) Applicant: Image Navigation Ltd., Jerusalem (IL)

(72) Inventors: Yuval Cohen, Moshav Kisalon (IL); Vered Cohen Sharvit, Modiin (IL); Uri Sonenfeld, Jerusalem (IL); Jeffrey Port, Neve Daniel (IL); Leonid Gootkin, Jerusalem (IL)

(73) Assignee: Image Navigation Ltd., Jerusalem (IL)

( * ) Notice: Subject to any disclaimer, the term of this patent is extended or adjusted under 35 U.S.C. 154(b) by 0 days.

(21) Appl. No.: 16/740,501

(22) Filed: Jan. 13, 2020

(51) Int. Cl.
| | | |
|---|---|---|
| *A61C 1/08* | (2006.01) | |
| *A61B 6/14* | (2006.01) | |
| *A61B 6/03* | (2006.01) | |
| *A61C 8/00* | (2006.01) | |
| *A61B 90/00* | (2016.01) | |

(52) U.S. Cl.
CPC .............. *A61C 1/084* (2013.01); *A61B 6/032* (2013.01); *A61B 6/145* (2013.01); *A61C 8/0089* (2013.01); *A61B 2090/3912* (2016.02); *A61B 2090/3916* (2016.02); *A61B 2090/3966* (2016.02); *A61B 2090/3983* (2016.02); *A61B 2090/3991* (2016.02)

(58) Field of Classification Search
CPC ....... A61C 1/084; A61C 8/0089; A61B 6/032; A61B 6/145; A61B 2090/3912; A61B 2090/3991; A61B 2090/3983; A61B 2090/3916; A61B 2090/3966
USPC .......................................................... 433/72
See application file for complete search history.

(56) References Cited

U.S. PATENT DOCUMENTS

| | | | | |
|---|---|---|---|---|
| 4,375,965 A | * | 3/1983 | Weissman ............ | A61C 9/0006 433/37 |
| 7,457,443 B2 | | 11/2008 | Persky | |
| 8,172,573 B2 | | 5/2012 | Sonenfeld et al. | |
| 9,402,691 B2 | | 8/2016 | Merritt et al. | |

(Continued)

FOREIGN PATENT DOCUMENTS

CN        108553186 A       9/2018

OTHER PUBLICATIONS

Block, Michael S. DMD et al. Static or Dynamic Navigation for Implant Placement—Choosing the Method of Guidance. American Association of Oral and Maxillofacial Surgeons. 2015. J Oral Maxillofac Surg: 1-9, 2015.

*Primary Examiner* — Matthew M Nelson
(74) *Attorney, Agent, or Firm* — Mark M. Friedman

(57) ABSTRACT

A stable affixation system for dental implantation includes a fixation tray having, for rapid placement, a housing defining a chamber whose inner surface is configured to house a flowable or malleable material (configured to harden) and be placed over one or more teeth during guided dental implantation surgery. A mechanism for urging the material against the teeth may comprise side walls having an inwardly directed extra flexible arm extension or an inwardly directed step. A lock mechanism may comprise a wedge positioned over the fixation tray to reduce or eliminate freedom of movement of the tray. For rapid removal, the system may include mechanisms (for example an element rotating inside the tray) for applying force on the tray and material and for ensuring that the material adheres more strongly to the tray than to the teeth. The system is sturdy enough to withstand forces including from various angles and leverage.

24 Claims, 16 Drawing Sheets

(56) References Cited

U.S. PATENT DOCUMENTS

| | | | |
|---|---|---|---|
| 9,622,837 B2 * | 4/2017 | Jansheski | A61C 9/0006 |
| 2002/0064753 A1 * | 5/2002 | Philp, Jr. | A61C 9/0026 |
| | | | 433/32 |
| 2010/0261133 A1 * | 10/2010 | Lax | A61F 5/566 |
| | | | 433/71 |
| 2011/0129796 A1 * | 6/2011 | Riggio | A61C 19/04 |
| | | | 433/171 |
| 2013/0224680 A1 * | 8/2013 | McDonald | A61C 9/0006 |
| | | | 433/38 |
| 2014/0272773 A1 | 9/2014 | Merritt et al. | |
| 2014/0343405 A1 * | 11/2014 | Daon | A61B 5/064 |
| | | | 600/424 |
| 2015/0150658 A1 * | 6/2015 | McDonald | A61C 9/0006 |
| | | | 433/38 |
| 2017/0290554 A1 | 10/2017 | Merritt | |
| 2018/0110596 A1 * | 4/2018 | Ackel | A61C 9/0006 |
| 2018/0206957 A1 * | 7/2018 | Ruth | A61C 9/0013 |
| 2019/0254776 A1 | 8/2019 | Habeb et al. | |

* cited by examiner

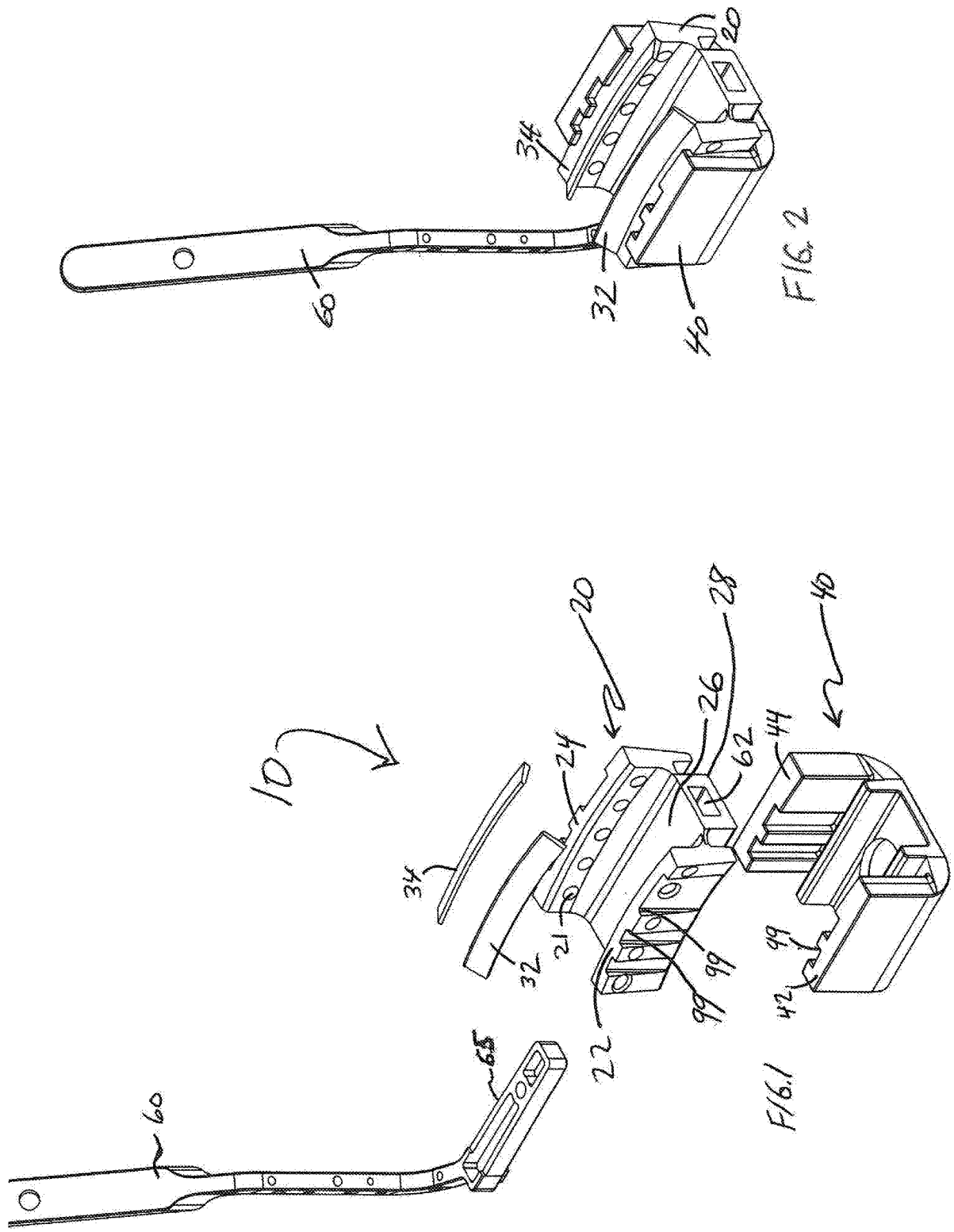

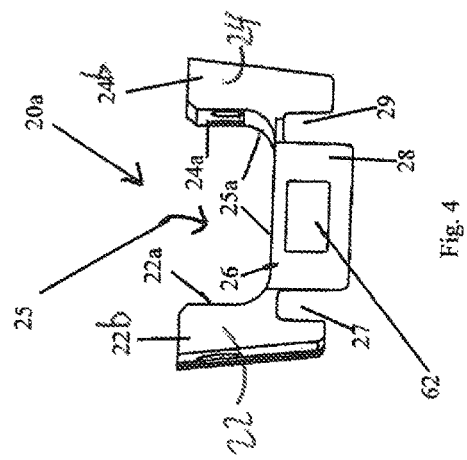
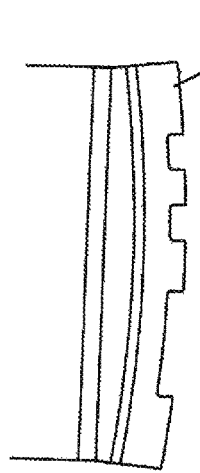
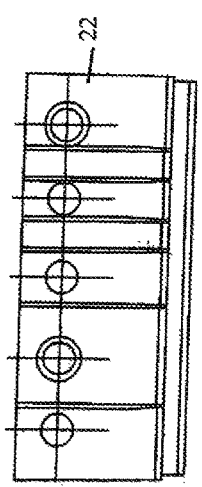
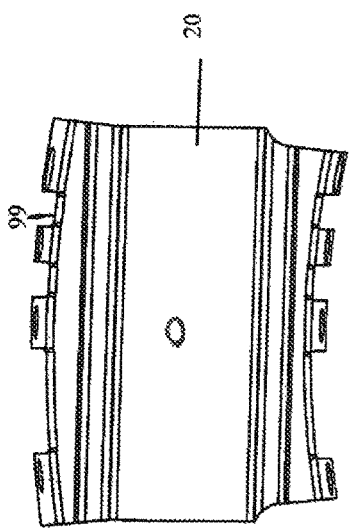

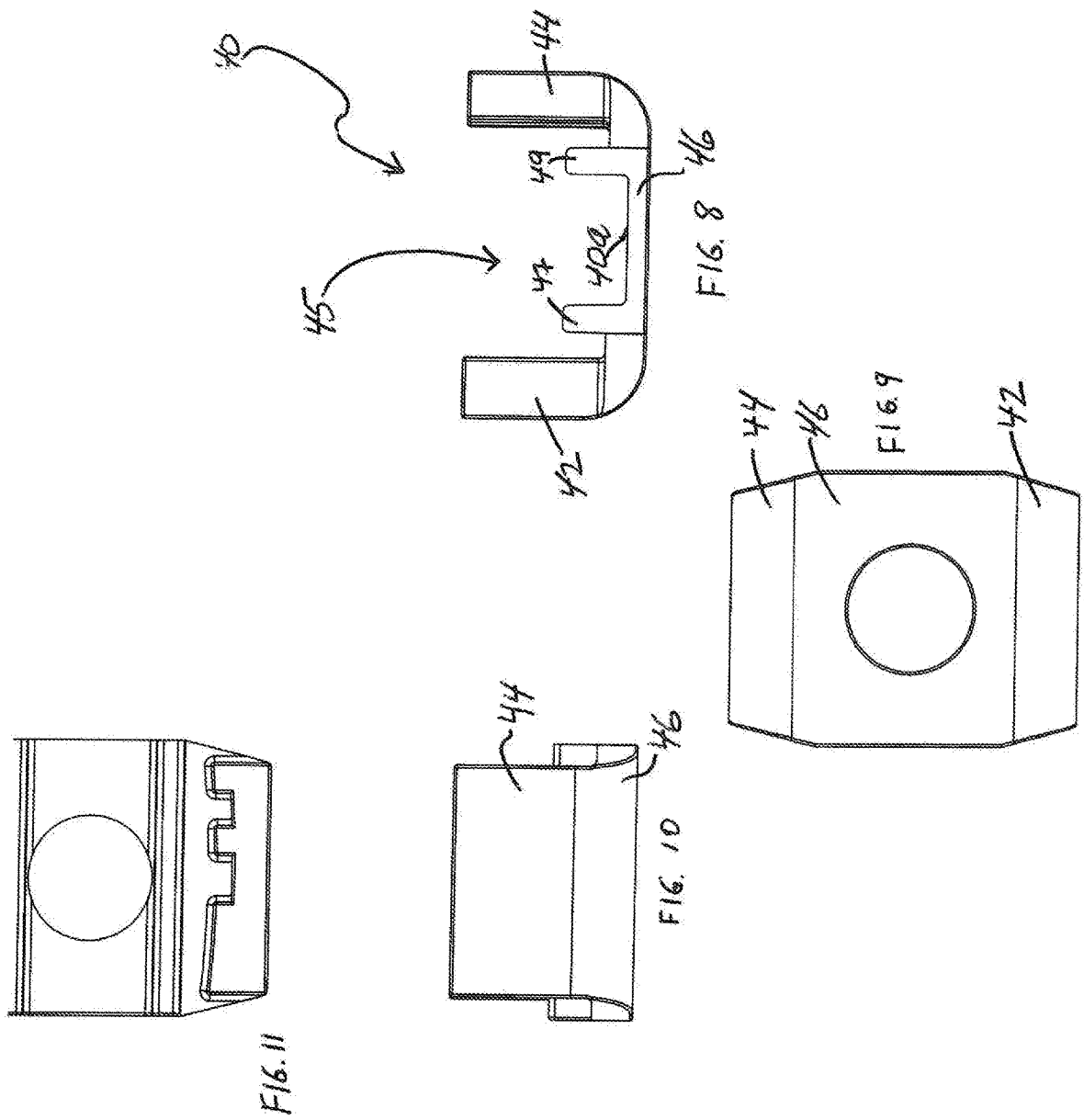

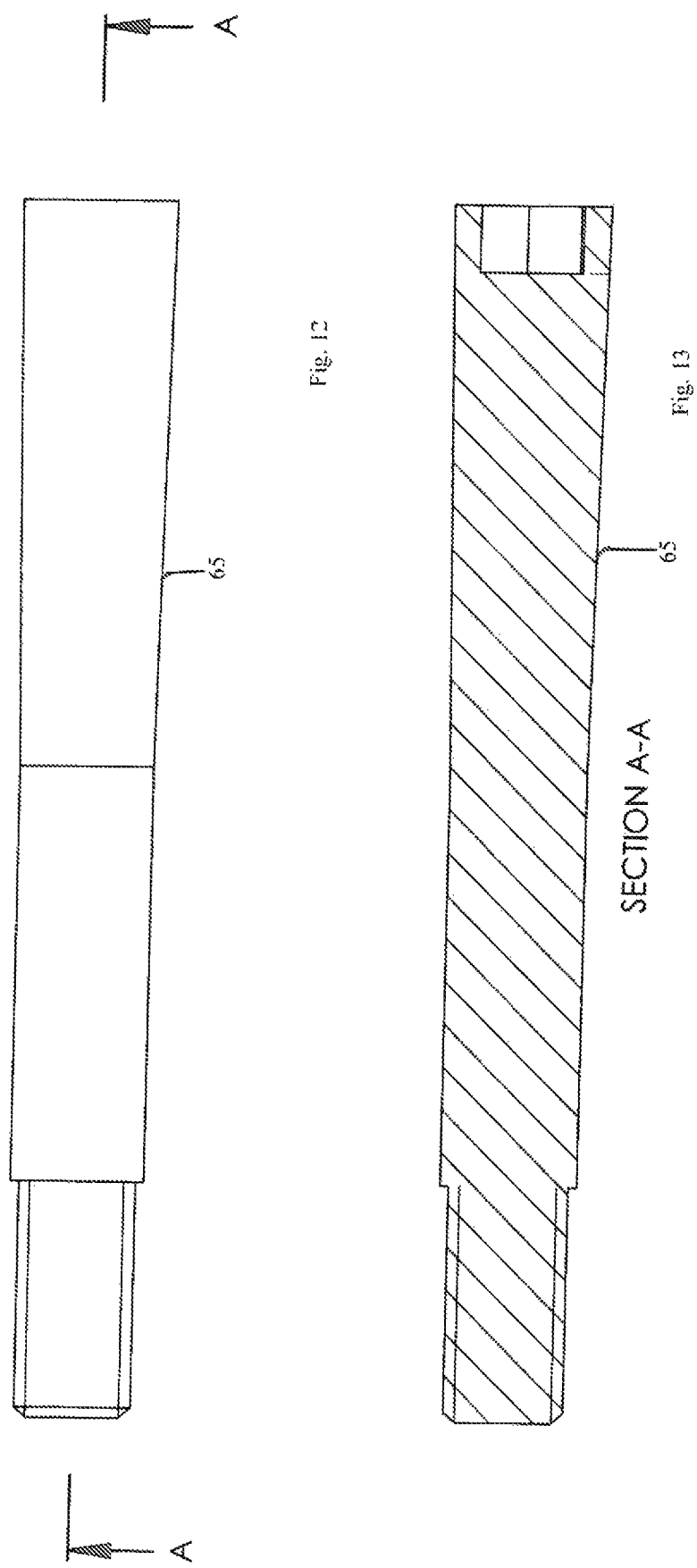

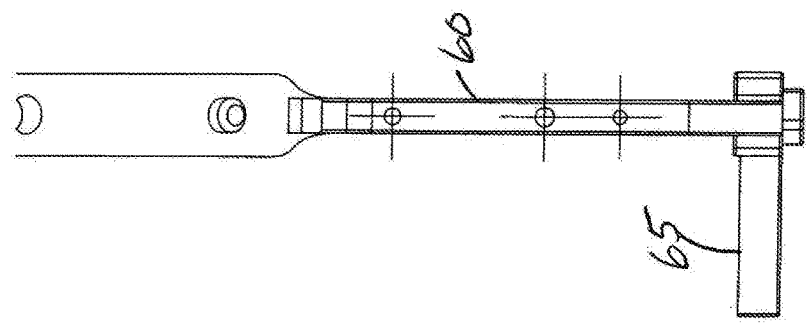
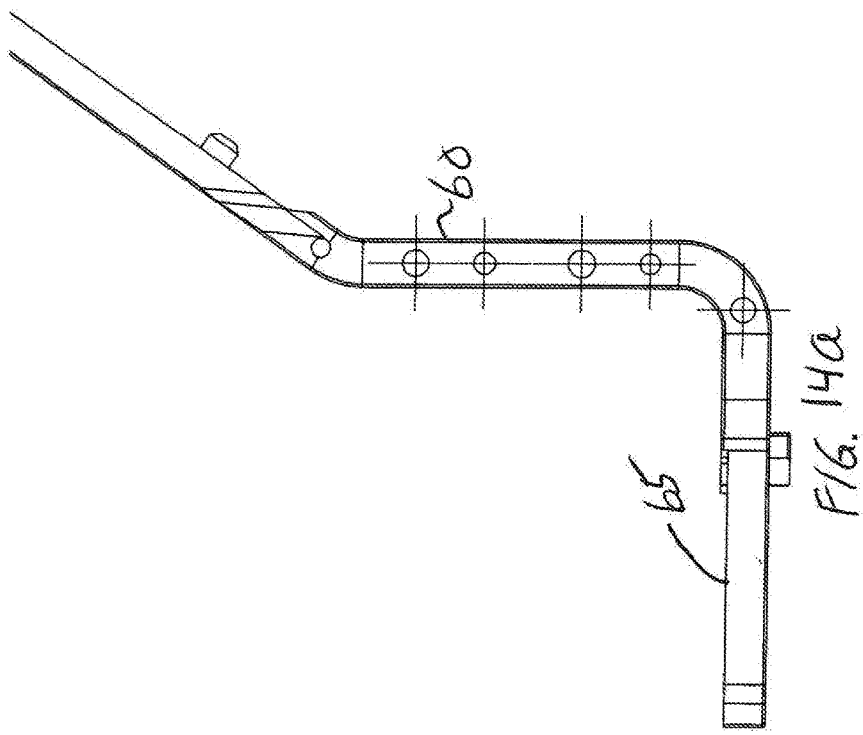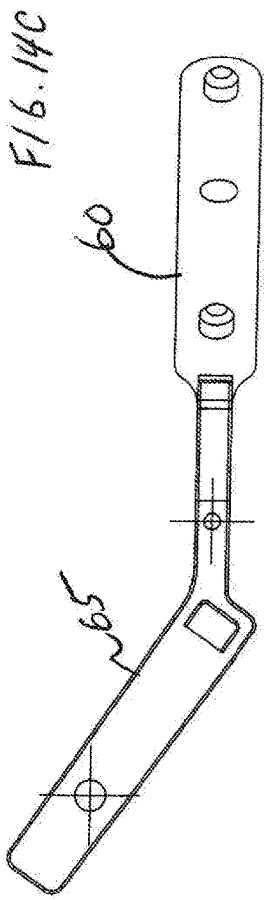

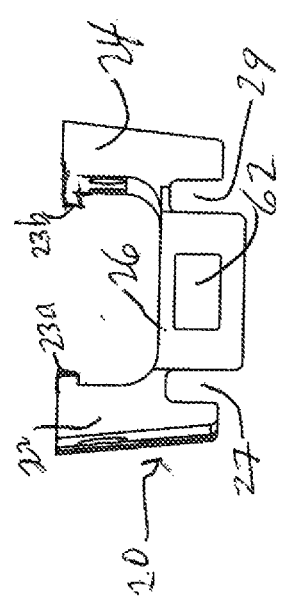

METHOD - 100

Deploying a fixation tray holding a flowable or malleable material over one or more teeth, the fixation tray having a housing defining a chamber and having a mechanism to urge the material against the one or more teeth

110

Locking the fixation tray to reduce or eliminate its freedom of movement

120

Allowing the flowable or malleable material to harden into a rigid but crisp state

130

Removing or unlocking the lock and then removing the fixation tray

METHOD - 200

Deploying a fixation tray holding a flowable or malleable material over one or more teeth, the fixation tray having side walls at least a portion of which are configured to flex under pressure, the side walls having extra flexible arm extensions inwardly facing to urge the flowable material
↓ 210

Locking the fixation tray to reduce its freedom of movement
↓ 220

Allowing the flowable or malleable material to harden into a rigid state
↓ 230

Removing or unlocking the lock and then removing the fixation tray by using a mechanism to exert a force on the fixation tray, thereby pressuring the at least a portion of the side walls to flex
240

FIG. 17

METHOD - 300

Deploying a fixation tray, whose housing defines a chamber holding a flowable or malleable material, over one or a plurality of teeth, the housing having sides at least a portion of which are configured to urge the material against the one or more teeth
310

Locking the fixation tray with a lock
320

Allowing the flowable or malleable material to harden
330

Removing or unlocking the lock and then removing the fixation tray by exerting a force on an element in an inside portion of the fixation tray so as to break the hardened material
340

FIG. 18

METHOD - 400

Deploying a fixation tray holding a flowable or malleable material over one or more teeth, the fixation tray having a housing defining a chamber and having a mechanism to urge the material against the one or more teeth
— 410

Locking the fixation tray to reduce or eliminate its freedom of movement
— 420

Allowing the material to harden and performing the guided surgery while the tray and lock remain in place in a sturdy and stable position
— 430

Removing or unlocking the lock and then removing the fixation tray
— 440

FIG. 21

STABLE AFFIXATION SYSTEM FOR GUIDED DENTAL IMPLANTATION

FIELD AND BACKGROUND OF THE INVENTION

The invention relates to affixation systems and more particularly to affixation systems for guided dental implantation surgery including a fixation tray configured to house a hardening material and including a lock.

Dental implants are used in cases where natural teeth are missing or have to be extracted. Dental implantation surgery involves drilling a hole and enlarging it to a specific size in the maxilla or mandible (upper or lower jaw bone) and then screwing in an implant, a screw-like object into the jaw. After the implant surgery, an abutment and crown are then placed.

The correct and accurate placement of the implant is very important for various reasons. There are anatomical structures which one does not want to drill into such as the inferior alveolar and mental nerves, maxillary sinuses or perforating bone. In addition, one does not want to drill into a tooth root or another implant. It is not easy to accurately position the implant "blindly" (only seeing the original access opening) around 8-13 mm deep into bone. Ideally, implants should be placed in a position and orientation so as to have biting forces in the long axis of the tooth. Improper placement might prevent achieving this Implants should be placed so as to leave a minimum of 2 mm of bone to prevent bone resorption. There is also an aesthetic component for the placement of implants especially in the anterior of the mouth, where the final aesthetic result is affected by the precise placement of the implant.

Originally, the only way to perform any surgery in general was freehand, without any guidance relating to the anatomical structures which one may encounter during surgery. In order to compensate for this, surgical access openings had to be large enough to allow visual verification. Laparoscopy as well as other guides has helped with this aspect in many types of surgeries.

In dentistry, utilizing guided dental surgery helps the surgeon follow the preplanned treatment plan. It makes the surgery minimally invasive, which reduces the risk of tissue damage and facilitates achieving the precision needed. Guided surgery is therefore a preferred approach for dental implant surgery.

During dental and certain other kinds of guided surgery there is a need for real-time computerized measurement of spatial position and orientation of specially marked objects, such as surgical instruments and implants to be implanted in pre-planned positions. The orientation and location of the surgical instruments is monitored by position sensors and the real-time location of the instruments can be displayed on previously acquired patient image data. The orientation and location of the patient is also typically tracked separately, to allow for sensing of anatomy movement relative to the tracked instruments during the operation. In dental surgery and in certain other surgeries, the various orientations and locations of the tracked objects need to be determined with great precision—in the case of dental surgery typically within an accuracy of less than a quarter of a millimeter.

SUMMARY OF THE INVENTION

One aspect of the invention is a stable affixation system for guided dental implantation, comprising a fixation tray customizable to the patient including a housing that defines a chamber configured to house a flowable or malleable material and be placed over one or a plurality of teeth of a person during the guided dental implantation surgery, the housing having sides, at least a portion of the sides are configured to flex under stress, the sides configured to urge the flowable or malleable material against the teeth; and a lock positioned on the fixation tray so as to reduce or eliminate a freedom of movement of the fixation tray.

In certain embodiments, the lock is a locking wedge positioned over the fixation tray. In certain embodiments, the locking wedge has an inner surface configured to define a chamber into which the fixation tray is configured to fit either snugly or using a friction fit.

In certain embodiments, the lock includes a mechanism for fixating at least side portions of the housing rigidly in place.

In certain embodiments, the housing includes a structure configured to join the flowable or malleable material, once hardened, to the housing such that a greater separation force is required to separate the flowable or malleable material, once hardened, from the housing, than a separation force required to separate the flowable or malleable material from the one or the plurality of teeth.

In certain embodiments, the lock is configured to reduce a freedom of motion of each a first side wall and of a second side wall of the fixation tray.

In certain embodiments, the housing comprises a pair of inclined, inwardly directed arm extensions that extend from an inner surface of the chamber. In certain embodiments, the housing is made from a first material and the arm extensions are made of a second material that is flexible.

In certain embodiments, the lock includes a first locking wedge side wall thicker than a flexible first side wall of the housing and a second locking wedge side wall thicker than a flexible second side wall of the housing.

In certain embodiments, the fixation tray has recesses and the lock has corresponding projecting members. In certain embodiments, the projecting members project from an underside of a locking wedge top portion of the lock. In certain embodiments, the recesses are planar recesses situated such that when the projecting members mate with the planar recesses, a first planar projecting member adjacent to and inward of a first side wall of the fixation tray and a second planar projecting member adjacent to and inward of a second side wall of the fixation tray.

In certain embodiments, the housing has an elongated cavity configured to receive a tracking element.

In certain embodiments, an end view of at least one of (i) the fixation tray or (ii) the lock is substantially U-shaped.

In certain embodiments, the housing includes arm extensions that are each configured to urge the flowable or malleable material to harden in an undercut of the one or the plurality of teeth to stabilize the system.

In certain embodiments, the fixation tray includes side walls and each of the arm extensions is more flexible than each of the side walls.

In certain embodiments, the housing has spaces configured to allow the flowable or malleable material to flow into and, once hardened, to lock into.

Another aspect of the invention is a method of using a stable affixation system during dental implantation, comprising deploying a fixation tray holding a flowable or malleable material over one or a plurality of teeth, the fixation tray having a housing defining a chamber configured to house the material and having sides at least a portion of which are configured to flex under stress, the sides configured to urge the flowable or malleable material against the one or the plurality of teeth; deploying a lock over the fixation tray, the lock configured to reduce or eliminate a freedom of movement of the fixation tray; allowing the flowable or malleable material to harden into a rigid but breakable state; removing the lock and then removing the fixation tray by exerting a force on the fixation tray to generate stress that breaks at least a portion of the hardened material.

In certain embodiments, exerting the force involves rotating an element in a cavity of the housing thereby breaking at least a portion of the hardened, previously flowable or malleable, material and allowing the at a portion of the sides of the housing to flex.

In certain embodiments, the method further comprises performing the guided dental surgery while the tray and lock remain in place in a sturdy and stable position.

In certain embodiments, the method further comprises rigidly attaching a connector to the tray and either (a) performing a computer tomography scan of the one or plurality of teeth before deployment of the fixation tray and before deployment of the lock and then after deployment of the tray and lock moving a tracking device along the one or a plurality of teeth to register the one or a plurality of teeth, or (b) performing a computer tomography scan of the one or plurality of teeth after deployment of the fixation tray and lock and a connector rigidly attached to the fixation tray then either (i) moving a tracking device along the connector to register the connector or (ii) rigidly attaching a tracking device to the connector to register the connector based on a physical relationship between the tracking device and the connector.

A still further aspect of the invention is a stable affixation system for guided dental implantation, comprising a fixation tray having a housing that defines a chamber configured to house a flowable or malleable material and be placed over one or a plurality of teeth of a person during the guided dental implantation surgery, the flowable or malleable material configured to harden into a crisp or brittle material so as to conform to a contour of the one or the plurality of teeth, the housing having a mechanism configured to urge the flowable or malleable material toward the one or the plurality of teeth; and a locking wedge positioned over the fixation tray so as to reduce or eliminate a freedom of movement of the fixation tray.

In certain embodiments, the housing includes a mechanism configured to join the flowable or malleable material, once hardened, to the housing such that a greater separation force is required to separate the flowable or malleable material, once hardened, from the housing, than a separation force required to separate the flowable or malleable material from the one or the plurality of teeth.

In certain embodiments, the housing has a mechanism configured to hold at least part of a tracking element and a mechanism configured to exert stress on the housing and/or on the crisp or brittle material so as to break at least a portion of the crisp or brittle material and dislodge the fixation tray from the one or the plurality of teeth.

A yet still further aspect of the invention is a stable affixation system for guided dental implantation, comprising a fixation tray customizable to the patient including a housing that defines a chamber configured to house a flowable or malleable material and be placed over one or a plurality of teeth of a person during the guided dental implantation surgery, the housing having sides, at least a portion of the sides are configured to flex under stress, the sides configured to urge the flowable or malleable material against the teeth, wherein the housing includes a locking mechanism configured to reduce or eliminate a freedom of movement of the fixation tray by reducing or eliminating an ability of the at least the portion of the sides of the housing to flex under stress.

In certain embodiments, the least a portion of the sides of the housing are configured to flex such that a further a portion of the sides is from a top portion of housing the more that portion of the sides spreads outward under stress.

In certain embodiments, the system further comprises a registration element configured to be rigidly attached to the tray.

These and other features, aspects and advantages of the invention will become better understood with reference to the following drawings, descriptions and claims.

BRIEF DESCRIPTION OF THE DRAWINGS

Various embodiments are herein described, by way of example only, with reference to the accompanying drawings, wherein:

FIG. 1 is an exploded view of a stable affixation system for dental implantation together with a pole with a connector to a patient tracking device, in accordance with an embodiment of the invention;

FIG. 3A is a view of a first of the arm extensions of the fixation tray of the stable affixation system from a side and an end, in accordance with an embodiment of the invention;

FIG. 4 is an end view of a fixation tray of the stable affixation system, in accordance with an embodiment of the invention;

FIG. 5 is a top view of a fixation tray of the stable affixation system, in accordance with an embodiment of the invention;

FIG. 6 is a side view of a fixation tray of the stable affixation system, in accordance with an embodiment of the invention;

FIG. 7 is a bottom view of a fixation tray of the stable affixation system, in accordance with an embodiment of the invention;

FIG. 8 is an end view of a locking wedge of the stable affixation system, in accordance with an embodiment of the invention;

FIG. 9 is a top view of a locking wedge of the stable affixation system, in accordance with an embodiment of the invention;

FIG. 10 is a side view of a locking wedge of the stable affixation system, in accordance with an embodiment of the invention;

FIG. 11 is a bottom view of a locking wedge of the stable affixation system, in accordance with an embodiment of the invention;

FIG. 12 is a side view of a pole of or used with the stable affixation system, in accordance with an embodiment of the invention;

FIG. 13 is a sectional view of the pole of FIG. 12 of or used with the stable affixation system, in accordance with an embodiment of the invention;

FIG. 14A is a side view of a tracking device and handle for the stable affixation system, in accordance with an embodiment of the invention;

FIG. 14B is a front view of a tracking device and handle for the stable affixation system, in accordance with an embodiment of the invention;

FIG. 14C is a further view of the tracking device and handle of FIGS. 14A-Fig. B;

FIG. 15 is an end view of one version of a fixation tray of the stable affixation system, in accordance with an embodiment of the invention;

FIG. 16 is a flow chart of a method, in accordance with an embodiment of the invention; and FIG. 17 is a flow chart of a method, in accordance with an embodiment of the invention;

FIG. 18 is a flow chart of a method, in accordance with an embodiment of the invention;

FIG. 21 is a flow chart of a method, in accordance with an embodiment of the invention;

DETAILED DESCRIPTION OF THE INVENTION

Figure 2A:
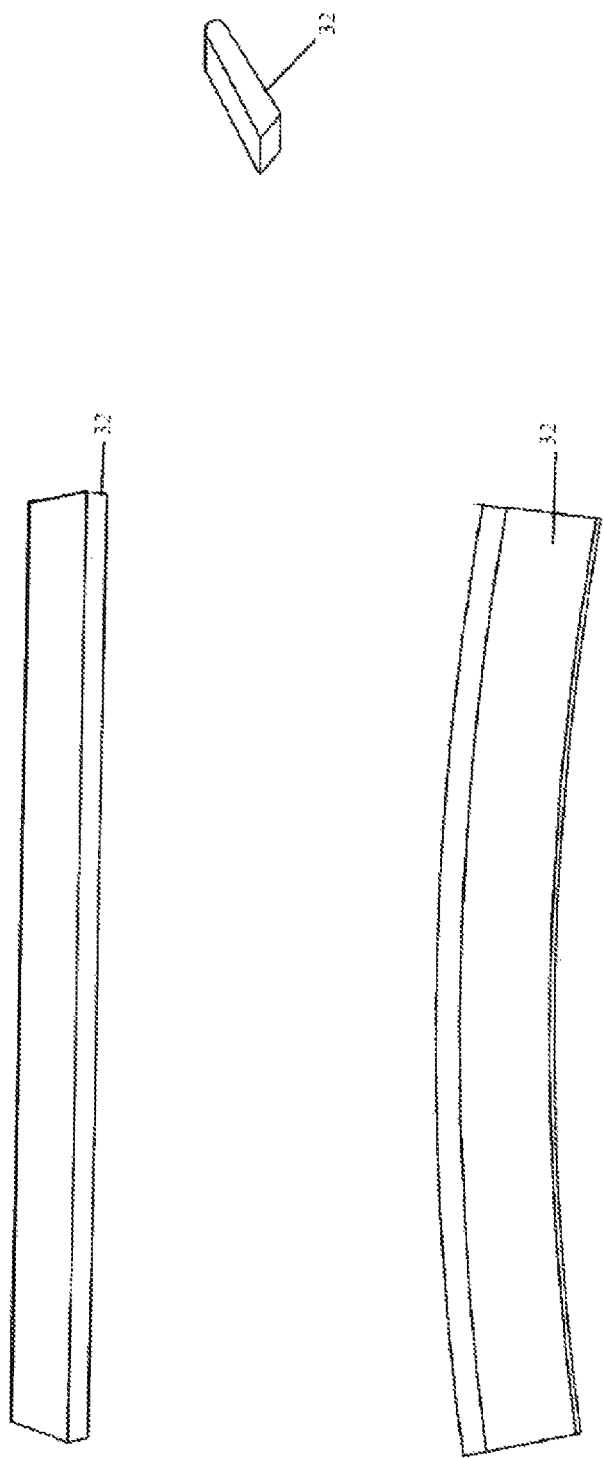
FIG. 2 is an assembled version of the stable affixation system of FIG. 1 together with the tracking device, in accordance with an embodiment of the invention.
Figure 3B:
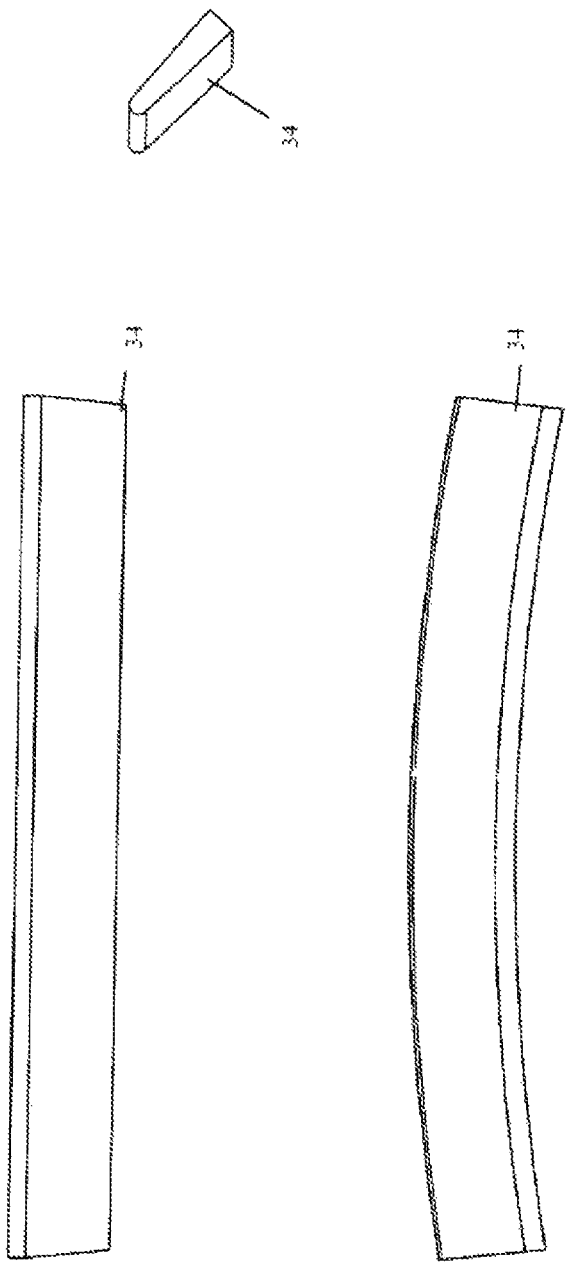
FIG. 3B is a view of a second of the arm extensions of the fixation tray of the stable affixation system from a side, in accordance with an embodiment of the invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The invention generally provides a stable affixation system for guided dental implantation, comprising in certain embodiments a fixation tray and a lock. In certain embodiments, the system is designed to be able to attach a tracking device that interacts with a guided dental implantation surgery system wherein such tracking device is kept immobile or at least immobile relative to the patient's mouth.

Certain embodiments of the invention utilize several principles that reflect advantages or requirements for affixation of tracking systems used during dynamic guided dental implant surgery. The first principle is fast and easy placement of a system that is customizable to the patient. The system should allow attachment of a tracker at an anatomical part of the subject such that the tracker and the anatomical part only move in exact conjunction with the surgical site. The second principle is stability of the system holding the tracker even in the face of significant force applied (against the tracker or its connector or against the system directly) including from a variety of angles and through leverage. The third principle is rapid removal of the system with limited force without damaging the teeth.

In certain embodiments, the principle of fast and easy placement is accomplished by a number of things including a fixation tray housing and a flowable or malleable material placed inside the housing which is effectively customizable to the particular patient's teeth because of the material being flowable or malleable. The second principle of stability is in certain embodiments accomplished by several things including the hardening of the flowable or malleable material, a lock mechanism (derived from features of the lock and features of the tray) which reduces or eliminates the freedom of movement of the tray and a mechanism to urge the material against the one or a plurality of teeth. The third principle of fast removal with limited force and without damaging the teeth is accomplished in certain embodiments by a number of things including: an easily removed lock mechanism; using a flowable or malleable material that hardens into a crisp or brittle material and providing the material inside a tray configured to break easily from forces or stress such as shear stress; a mechanism for generating forces or stress (such as shear stress) on the tray and on the material inside the tray; providing that the separation force needed to separate the material from the tray is greater than the separation force needed to separate the already hardened material from the teeth so that the material is removed with the tray and does not stay attached to the teeth when the tray is removed; and using a tray whose housing has at least a portion or portions or areas or points configured to flex under stress (in some embodiments this flexing leads to breakage also of the tray under this stress).

The fixation tray may have a housing that defines a chamber whose inner surface is configured to house a material that is a flowable or malleable material so that the housing in effect becomes customizable to the individual patient's teeth. The feature of the housing having portions that flex under stress facilitates dislodging of the fixation tray.

In one implementation of the housing of fixation tray, the fixation tray may have side walls and a fixation tray top portion that may connect a first side wall with a second side wall of the fixation tray. In certain embodiments, these side walls or portions thereof are configured to flex at least to some extent under stress or pressure. In some cases, these side walls have arm extensions that are significantly more flexible than any other part of the fixation tray including than the first and second side walls, for example because in some embodiments the arm extensions are made of a different material, in one non-limiting example silicone, than the side walls themselves. The extra flexibility of the arm extensions in some embodiments is due to manufacturing considerations but the arm extensions help urge the flowable or malleable material housed by the fixation tray inwardly toward the teeth and may render the fixation tray adaptable to fit more jaw and teeth sizes. This extra flexibility also makes manufacturing the fixation tray easier in certain embodiments. In other cases, the side walls of the fixation tray have an inwardly-directed pair of steps at or near a free end of the side walls or at another position along the side walls.

The affixation system also includes a lock which in certain embodiments is implemented as a locking wedge configured to be placed on the fixation tray in order to reduce or eliminate the freedom of movement of the fixation tray that would otherwise occur from forces on the tray (or from forces on the tracking device (not shown) or the connector of the tracking device that in turn exerts force on the tray) while the tray is positioned on the teeth during the guided dental implantation surgery.

After the flowable or malleable material hardens into a rigid state in a crisp form, one may rapidly remove the affixation system by for example removing the locking wedge followed by exerting a force in the tray such as a force on an element situated in a cavity of the housing (for example a pole that can be rotated within the cavity). The force may be exerted on the element to generate forces or pressure or stress such as shear stress to break at least a portion of the hardened material for example on an occlusal surface of the plurality of teeth and to cause the all or a portion of the sides of the housing (including any arm extensions or steps) to flex so that the fixation tray can be dislodged and removed from the one or the plurality of teeth. If a step is used instead of extra flexible arm extensions, the whole first and second side wall or the sides or side portions of the housing together with the step would flex somewhat due in one example to recesses alongside the side walls or side portions of the housing.

In certain embodiments, the affixation system is configured to be rapidly placed on the one or plurality of teeth, is configured to be rapidly removed from the one or plurality of teeth and/or is configured to be maintained in position in a stable and secure manner (due in part to the locking mechanism) in the face of significant weight or force applied at any of a variety angles including such force applied through leverage.

The principles and operation of a Stable Affixation System for Guided Dental Implantation may be better understood with reference to the drawings and the accompanying description.

As shown in FIGS. 1-15, especially FIGS. 1-2, 4-5 and 8, one embodiment of the invention is a stable affixation system 10 for guided dental implantation that comprises a fixation tray 20 that in certain embodiments has a housing 20a that defines a chamber 25 configured to house a flowable or malleable material (not shown) and be placed over one or a plurality of teeth of a person during guided dental implantation surgery. The use of the flowable or malleable material that hardens so as to conform to the shape of the tooth or teeth of the patient facilitates customizing system 10 (and in particular the housing 20a of tray 20) for the individual patient. This facilitates rapid positioning of system 10 on the one or more teeth of the patient.

The mechanism for rapid positioning of system 10 onto the individual patient's teeth may also be implemented at least in part by providing housing 20a with a mechanism for urging the flowable or malleable material against the one or the plurality of teeth. Accordingly, in certain embodiments, housing 20a may have a pair of inwardly directed arm extensions 32, 34 (FIGS. 1-3B) or a pair of inwardly directed steps 23a, 23b (FIG. 15) that extend from an inner surface 25a of chamber 25, each arm extension 32, 34 or step 23a, 23b of the pair configured to urge the flowable or malleable material against the one or more teeth.

Although FIG. 4 depicts housing 20a (and in particular inner surface 25a of chamber 25 defined therein) to include straight portions of its walls, this is only one non-limited implementation and in other embodiments housing and in particular inner surface 25a of the chamber 25 can have round or curved walls or borders. Housing 20a defining chamber 25 may include side portions that may be rounded or straight or a combination of the two. In one implementation, housing 20a (as well as chamber 25) includes a first side wall 22, a second side wall 24 and a fixation tray top portion 26 that connects the two side walls 22, 24. Side walls 22, 24 may be straight or curved or a combination. In one version shown in FIG. 4, housing 20a comprises substantially side walls 22, 24 that have straight portions and rounded portions excluding any arm extensions 32, 34 or steps 23a, 24b.

In certain embodiments, the purpose of fixation system 10 is to be able to attach a tracking system that does not move—or at least does not move relative to the patient's mouth—during the guided dental implantation surgery. To this end, in one non-limiting implementation, fixation tray 20 may have a portion such as a top portion 26 of housing 20a (for example including a holder 28 which is an area of top portion 26) that defines within it (i.e. within holder 28) a cavity, for example an elongated cavity 62, configured to receive a tracking device (not shown) or a handle and/or a connector 60 that connect to such a tracking device. The tracking device may be used during dental implantation surgery. Connector 60 may in some embodiments be made of titanium and may also connect to a registration device or connector 60 itself may be a registration device or part of one. In the embodiment shown in FIG. 1 and FIG. 2, connector 60 connects to tray 20 using pole 65 situated at a first end of connector 60 and connects to the tracking device at the other end of connector. It should be understood that the pole 65 is a non-limiting example of how connector 65 can connect to tray 20 and many other examples are possible with components of other shapes. In addition, the term "pole" is not intended to suggest being cylindrical although it can be.

When lock 40 or locking wedge 40 is not deployed onto fixation tray 20, at least a portion of housing 20a such as side walls 22, 24 are configured to flex under stress. In some embodiments, housing 20a may also be configured to flex under stress at least to some extent from the fact that it defines an open chamber (until the flowable or malleable material hardens into a rigid state). One further way of rendering portions of housing 20a (for example side walls 22, 24) able to flex under stress is to incorporate at least one recess for example at least one recess in the wall of the housing 20a such as recess 27 alongside first side wall 22 and recess 29 alongside second side wall 24. Recesses 27, 29, in one non-limiting embodiment are planar recesses between the respective side wall and a portion of top portion 26, for example holder 28. Other configurations of recesses are also possible in which recesses 27, 29 are not planar. Other ways of making portions of housing 20a configured to flex under stress are also contemplated such as from the nature of the material that housing 20a is made from. In some versions housing 20a is cylindrical thereby requiring only a single recess.

In certain embodiments, portions of housing 20a, for example side walls 22, 24 are configured to flex under stress such that free ends 22b, 24b of walls 22, 24 spread outward, or at least spread outward more than portions of housing 20a closer to top portion 26. This could occur, for example, as a result of a clamping motion at the other ends of the side walls 22, 24 caused by lock 40 or locking wedge 40.

In versions where housing 20a includes a fixation tray top portion 26 configured to connect first and second side walls 22, 24, then the inner surface 25a of chamber 25 may be defined by an inner surface of tray top portion 26 together with an inner wall surface 22a, 24a of each of the first and second side walls 22, 24. Chamber 25 is configured to house the flowable or malleable material (not shown) which as part of tray 20 may be placed over one or a plurality of teeth (not shown) of a person during guided dental implantation surgery.

In one embodiment, first side wall 22 and the second side wall 24 are each made of a first material and each side wall 22, 24 has an arm extension 32, 34 that is more flexible than side wall 22, 24. Arm extensions 32, 34 may be configured to urge the flowable or malleable material against the one or the plurality of teeth.

The flowable or malleable material, in some embodiments, is of the type of material used for temporary crowns. In one non-limiting example, the flowable or malleable material is highly viscous akin to the viscosity of ketchup (5000-20000 mPa·s at 25° C.) or peanut butter ($10^4$ to $10^6$ mPa·s) or even pitch ($2.3 \times 10^{11}$) and in another example has low viscosity akin to that of whole milk (2.2 mPa·s at 20° C.)

or even akin to anything with more viscosity than water (1 at 20° C.) or anything in between any of these ranges. In any event, the flowable or malleable material is not only configured to harden but is also configured to harden into a crisp or brittle material that may be easily breakable in response to the stress, especially in response to shear stress, since this is necessary when one wants to dislodge the fixation tray 20 from the one or plurality of teeth.

In one embodiment, arm extensions 32, 34 extend from each side of housing 20a, for example by extending from each of side walls 22, 24 of housing. In one implementation, arm extensions 32, 34 extend from a free end of side walls 22, 24 respectively (i.e. arm extension 32 extend from a free end of side wall 22 and arm extension 34 extending from a free end of side wall 24). In another embodiment, arm extensions 32, 34 extend from a point adjacent the free end of side walls 22, 24 respectively. In other embodiments, arm extensions 22, 24 extend from a point a few millimeters (1 or 2 or 3 mms) above the free end of side walls 22, 24. In some embodiments, arm extensions extend from a midpoint or a different portion of each of side walls 32, 34. In certain embodiments shown in FIGS. 1-2, arm extensions 32, 34 are inwardly directed. In certain embodiments, arm extensions 32, 34 are also inclined, in one non-limiting example inclined at an angle between 30° and 60° (for example between) 40°-50° relative to side walls 22, 24 respectively (or relative to sides of housing 20a or sides of inner surface 25a of chamber 25). The free ends 22b, 24b, of side walls 22, 24 refer to the end furthest from top portion 26 that in some embodiments connects the side walls 22, 24.

Arm extensions 32, 34 may be made of a material different from the rest of fixation tray 20, for example different from housing 20a or different from side portions of housing 20a or different from the remainder of each side wall 22, 32. For example, in one embodiment arm extensions 32, 34 are made of silicone and the silicone is flexible (and more flexible than any other part of the fixation tray 20 or housing 20a. The fact that arm extensions 32, 34 are inwardly directed and in some case also inclined helps push or urge the flowable or malleable material toward the one or more teeth and helps the fixation tray 20 fit more jaw and teeth sizes. Arm extensions 32, 34 are each configured to form alongside an undercut of the one or more teeth and urge the flowable or malleable material to adhere closely to the anatomical formation of the one or more teeth and into the undercuts so that when this material hardens into a rigid state it in effect grips the one or the plurality of teeth at the undercut of the one or the plurality of teeth. This increases the stability of system 10 in that the entire system 10 not only cannot be dislodged as a unit but in fact is substantially immobile during the dental surgery.

As a result, there is no realistic option to pull the tray 20 plus hardened material straight vertically up off the teeth.

By using a tray 20 having at least portions or a portion that is configured to flex under stress, and by using a flowable or malleable material that once hardens is crisp or brittle, the hardened material in chamber 25 breaks when pressure is exerted (for example by rotating an element, such as pole 65 of connector 60, in cavity 62 of top portion 26 of tray 20) because the force from rotating element 65 generates pressure or stress against fixation tray 20 that translates into stress (such as shear stress) or pressure against the hardened material which breaks it and makes it break away from the teeth (since the hardened material is strongly attached to tray 20). Thus, the hardened material comes off with the tray 20 when the fixation tray 20 is dislodged. If the tray were rigid and not configured to flex under stress, the stress exerted against the tray would not cause the hardened material to break and exerting a force on tray 20 would pressure the tooth or teeth themselves and may simply break or take out the whole tooth or teeth.

In certain embodiments, the housing includes a mechanism or structure configured to join the flowable or malleable material, once hardened, to the housing such that a greater separation force is required to separate the flowable or malleable material, once hardened, from the housing, than a separation force required to separate the flowable or malleable material from the one or the plurality of teeth. In one non-limiting implementation of this mechanism or structure, fixation tray 20, and in particular housing 20a, may have holes 21 (FIG. 1) (or spaces that assume other shapes such as elongated or otherwise) configured to allow the flowable or malleable material to flow into, and when hardened lock into. This way, when the fixation tray 20 is dislodged, the hardened material (formerly flowable or malleable material) breaks with it and dislodges from the teeth. This facilitates rapid removal of the system with limited force and without damaging the teeth. Although FIG. 1 depicts one non-limiting implementation in which one or more holes 21 are situated in side walls 22, 24 of housing 20a of fixation tray 20, it is contemplated that in other implementations, the one or more holes 21 or spaces of other shapes may be situated in other portions of fixation tray 20 such as the top portion 26 of fixation tray. In another non-limiting implementation of this mechanism, the flowable or malleable material is configured by the type and nature of the material itself to adhere to a stronger degree to the material from which the housing of tray 20 is made than the degree to which the flowable or malleable material (once hardened) adheres to the one or the plurality of teeth.

Note that as seen in FIG. 1, tray 20 is upside down relative to how it would be placed on a patient's lower tooth or teeth and right side up in terms of how it would be placed on a patient's upper tooth or teeth. Hence, for convenience, the phrase "placed over" or "deployed over" or "placed on" or "positioned on" one or a plurality of teeth as used in this patent application should be understood broadly to describe both placing, deploying or positioning the tray 20 over a patient's lower teeth (or tooth) as well as placing, deploying or positioning or affixing tray 20 under the patient's upper teeth. Likewise, in this patent application when it is stated that the lock 40 or locking wedge 40 is placed or deployed "over" or "on" tray 20, the word "over" and the word "on" in this context should be understood broadly to also encompass scenarios where the system is applied to upper teeth and the lock 40 or wedge 40 is affixed to the tray 20 by placing lock 40 or wedge 40 under tray 20 when the tray 20 is held in a position secured to (or in position to be secured to) the upper teeth.

As seen from FIGS. 1-2 and 8-11, fixation system 10 may also comprise a lock 40 positioned on tray 20 (which may be implemented in one embodiment as a locking wedge 40 positioned on or over the fixation tray 20) so as to reduce or eliminate a freedom of motion or movement of housing 20a or of all or part of side portions of housing 20a or of sides or of first and second side walls 22, 24 of housing 20a of fixation tray 20. Lock 40 or Locking wedge 40 is configured with some mechanism designed to fixate housing 20a or at least side portions of housing 20a rigidly in place. In one implementation, lock 40 or locking wedge 40 is configured to fixate side walls 22, 24 rigidly in place.

In certain embodiments of locking wedge 40, locking wedge 40 has an inner surface 40a (FIG. 8) configured to define a chamber 45 into which the fixation tray 20 is configured to be emplaced or to be fit. For example, inner surface 40*a* may be configured such that tray 20 for example fits into chamber 45 snugly or for example fits into chamber 45 using a friction fit or under pressure.

In one non-limiting implementation of the mechanism to fixate or remove the flexibility of the housing 20*a* or of at least of a portion of housing 20*a*, locking wedge 40 may include a first locking wedge side wall 42 thicker than the first side wall 22, a second locking wedge side wall 44 thicker than the second side wall 24 and may also include a locking wedge top portion 46 configured to connect the first and second locking wedge side walls 42, 44. FIG. 9 is a top view that depicts sides 44, 46 of wedge 40 as if splayed outward but this view is not intended as a realistic depiction.

As noted and as seen from FIG. 4, fixation tray 20 or its top portion 26 may in certain embodiments have a recess 27 situated alongside side wall 22 for example alongside a protruding top portion of first side wall 22 and a recess 29 situated alongside side wall 24 for example alongside a protruding top portion of second side wall 24. FIG. 4 does not show and is not intended to depict any arm extensions 32, 34 or any steps 23*a*, 23*b* that housing 20*a* may have.

As seen from FIG. 8, locking wedge top portion 46 in certain embodiments has projecting members 47, 49 that are configured to mate with or fit inside at least a portion of recesses 27, 29 respectively, as seen also from FIG. 1. For example, locking wedge top portion 46 may have planar projecting members 47, 49 that correspond to planar recesses 27, 29 in certain embodiments. In other embodiments, recesses 27, 29 fit together with projecting members 47, 49 without either of them being planar. Projecting members 47, 49, which may be planar, may project from an underside of the locking wedge top portion 46.

As seen from FIGS. 1-2, 4 and 8, in one embodiment, planar recesses 27, 29 are situated such that when the planar projecting members 47, 49 mate with the planar recesses 27, 29, a first planar projecting member 47 is adjacent to and inward of the first side wall 22 of the fixation tray 20 and a second planar projecting member 49 is adjacent to and inward of the second side wall 24 of the fixation tray 20.

In certain embodiments of system 10, there is a structural means of snapping or locking or fitting together by friction fit or otherwise fixedly connecting locking wedge 40 to fixation tray 20. In one non-limiting implementation of this connection shown in FIG. 1, FIG. 5 and FIG. 11, both fixation tray 20 and locking wedge 40 have ridges 99 on portions of their side walls. For example, as shown in FIGS. 1, 5, 11, outer surfaces of side walls 22, 24 of fixation tray 20 and inner surfaces of side walls 42, 46 of wedge 40 have corresponding or matching ridges 99.

When locking wedge 40 is placed on fixation tray 20, locking wedge 40 is configured to reduce or eliminate a freedom of movement of each of the first side wall 22 and the second side wall 24 of fixation tray 20. In one non-limiting example, locking wedge 40 is configured to reduce a freedom of movement of each of the first side wall 22 and the second side wall 24 by 40% (or by at least 40%) or in other embodiments by 50% (or by at least 50%) or in other embodiments by 70% (or by at least 70%) or in still other embodiments by 90% (or by at least 90%) or in still other embodiments by a particular percent between 40% and 95%.

As can be seen from FIG. 4 and FIG. 8 an end view of at least one of (i) the fixation tray 20 or (ii) the locking wedge 40 is substantially U-shaped. Although FIG. 4 does not include arm extensions 32, 34, even with arm extensions 32, 34 (see FIG. 2) tray 20 may be considered substantially U-shaped.

Figure 19:
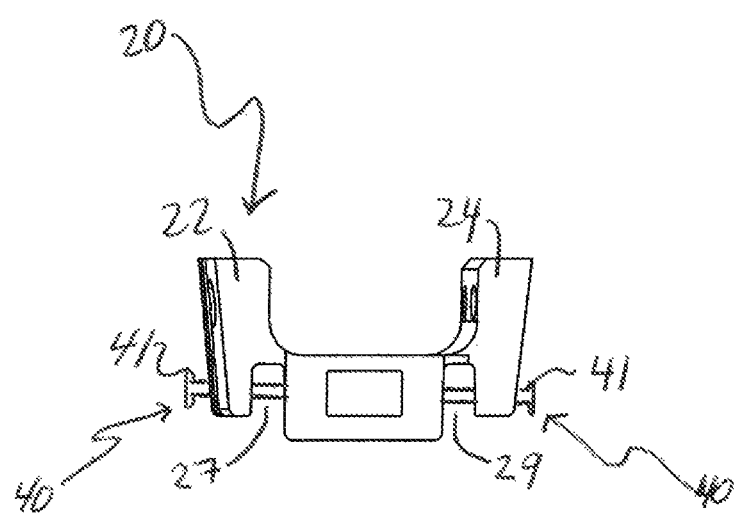
FIG. 19 is a schematic of a lock mechanism applied to FIG. 4, in accordance with an embodiment of the invention.
Figure 20:
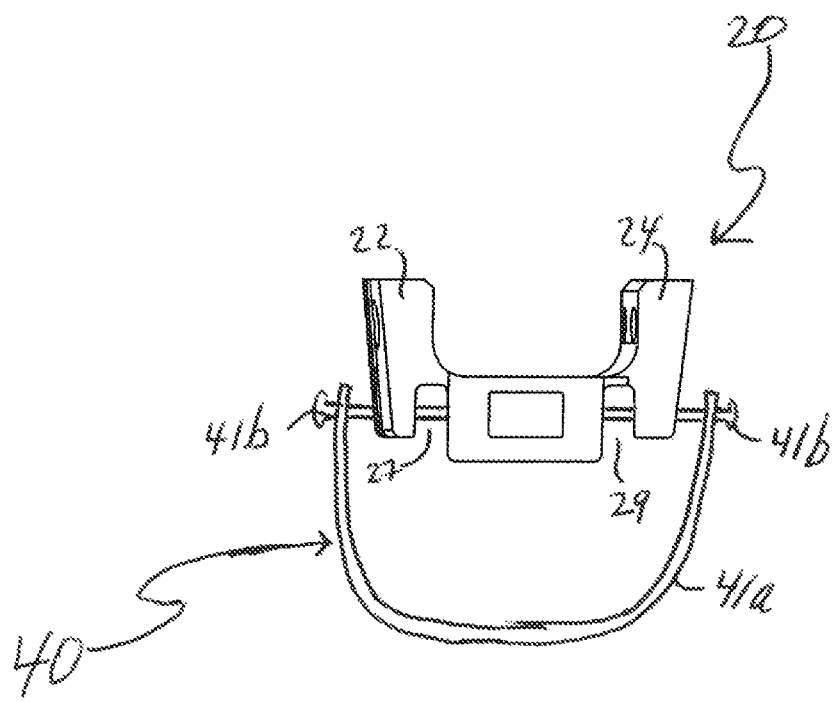
FIG. 20 is a schematic of another lock mechanism applied to FIG. 4, in accordance with an embodiment of the invention.
Figure 22:
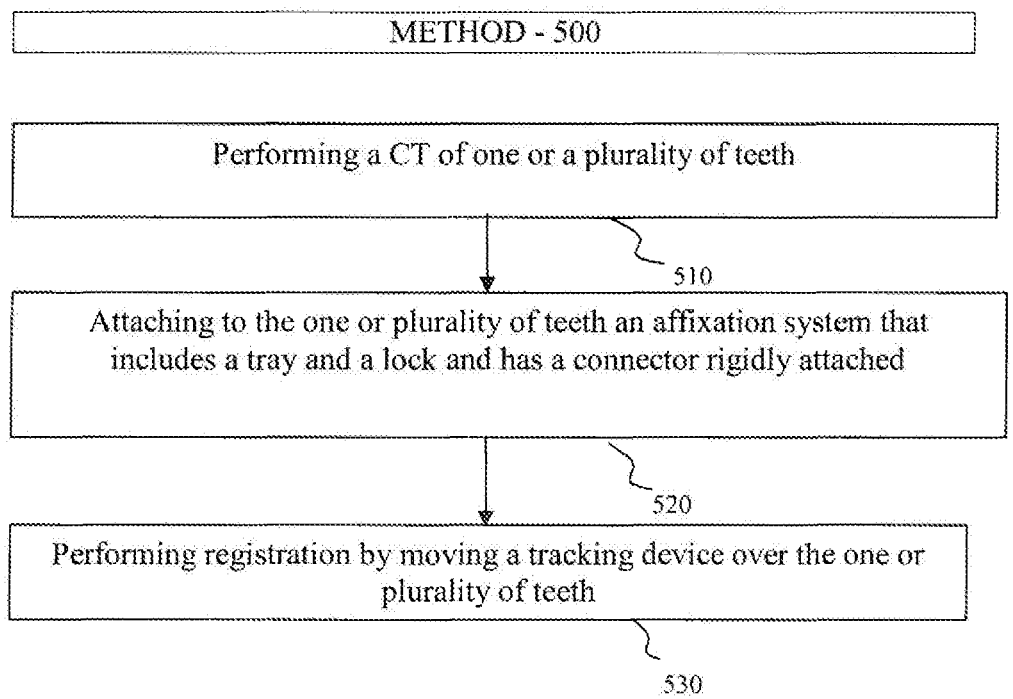
FIG. 22 is a flow chart of a registration method, in accordance with an embodiment of the invention.
Figure 23:
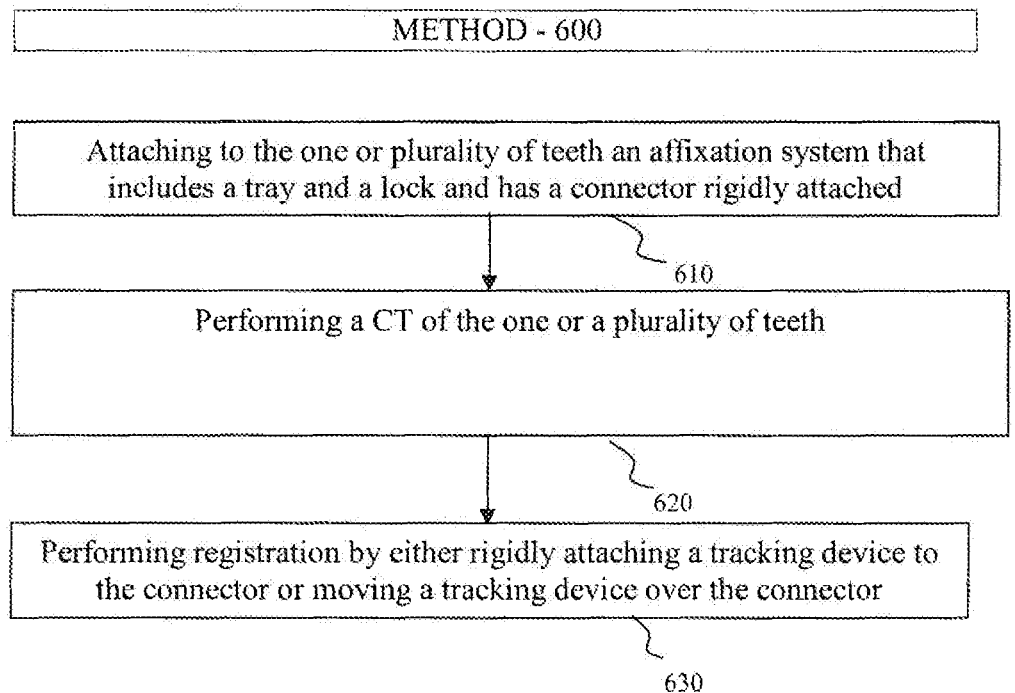
FIG. 23 is a flow chart of another registration method, in accordance with an embodiment of the invention.

In another implementation of lock 40 shown in FIG. 19 and FIG. 20, the housing 20*a* includes locking mechanism 40 configured to reduce or eliminate a freedom of movement of the fixation tray 20 by reducing or eliminating an ability of the at least the portion of the sides of the housing to flex under stress. In one non-limiting example, lock 40 comprises a clamp 41*a* and/or a fastener 41*b* (i.e. screw 41*b* or a pair of screws 41*b*) integrated with the tray 20 (or in other versions not integrated with the tray 20) such that adjustment of the clamp 41*a* and/or screw(s) 41*b* is configured to reduces or eliminates the ability of housing 20*a* to flex under stress. In one implementation of this example, the clamp 41*a* and/or screw(s) 41*b* is configured to accomplish this by locking side walls 22, 24 of housing 20*a*, for example by traversing recesses 27, 29. Another implementation of lock 40 is similar to FIG. 20 except that there are no recesses 27, 29 in tray 20 and the clamp 41*a* is positioned to grip tray 20 further down, that is further from top portion 26 and close to free ends of side walls 22, 24 (or at least closer to free ends of side walls 22, 24 than shown in FIG. 20). In that case, lock 40 may also comprise screw(s) 41*a* (although in other versions clamp 41*a* operates without screws 41*b*).

Accordingly, one particular embodiment of the invention is a stable affixation system 10 for guided dental implantation, comprising a fixation tray 20 customizable to the patient including a housing 20*a* that defines a chamber 25 configured to house a flowable or malleable material and be placed over one or a plurality of teeth of a person during the guided dental implantation surgery, the housing 20*a* having sides, wherein at least a portion of the sides are configured to flex under stress, the sides configured to urge the flowable or malleable material against the teeth, and wherein the housing 20*a* includes a locking mechanism 40 configured to reduce or eliminate a freedom of movement of the fixation tray by reducing or eliminating an ability of the at least the portion of the sides of the housing 20*a* to flex under stress. In some versions, the least a portion of the sides of the housing are configured to flex such that a further a portion of the sides is from a top portion of housing the more that portion of the sides spreads outward under stress. In some versions, the system 10 further comprises a registration element 60 configured to connect to tray 20. In that case, system 10 includes that which is necessary for the tray and lock 40 to be registered for purposes of the guided surgery. The registration element is configured to align for a computer navigation system used during the surgery the exact CT coordinates with the exact real world coordinates of a registered body rigidly attached to (or forming part of) system 10.

As seen from the flow chart of FIG. 16, one embodiment of the invention is a method 100 of using a stable affixation system during dental implantation. Method 100 may comprise a step 110 of deploying a fixation tray 20 holding a flowable or malleable material over one or a plurality of teeth, the fixation tray having a housing 20*a* wherein at least a portion such as side portions of housing 20*a* (in one implementation side walls (for example a first side wall 22 and a second side wall 24)) are configured to flex under stress. There may also be a fixation tray top portion 26 configured to connect the first and second side walls. The housing 20*a* defines a chamber 25 and may have any of the structures described with respect to any of the embodiments of fixation tray 20 or system 10. For example, housing 20*a* may have an element such as extra flexible arm extensions, for example arm extensions that are inwardly facing (and that may be inclined) to urge the flowable or malleable material against the one or more teeth. For example, arm extensions 32, 34 may extend from a free end or a point adjacent to a free end of, or may extend from a different part of, each of the first and second side walls (or side portions of housing 20a) as inclined inward-directed arm extensions configured to urge the flowable or malleable material against the one or the plurality of teeth. In some embodiments, the step 110 of deploying may be accomplished rapidly and easily.

Method 100 may also include step 120 of locking the fixation tray such as by a lock 40 or by deploying a locking wedge over the fixation tray, for example a locking wedge 40 that is configured to fixate tray 20 in place or grip fixation tray 20 and/or reduce or eliminate its freedom of movement. The mechanism for reducing or removing the freedom of movement of tray 20 or fixating tray 20 in place may be any suitable mechanism for example any mechanism described with regard to system 10 or tray 20. In some embodiments, the step 120 of locking effectuates a stable and sturdy system to which a tracking device may be attached and which is stable in the face of significant force applied from any of a variety of angles and using leverage. Step 120 may also include locking an element such as pole 65 for example by using a fastener or screw that traverses both a hole in lock 40 and a hole in tray 20 (see FIG. 1, FIG. 5, FIG. 9).

Step 130 of method 100 may comprise allowing the flowable or malleable material to harden, for example to harden into a rigid but crisp or brittle state, for example a crisp or brittle state that is easily breakable upon application of a force or stress such as shear stress. The flowable or malleable material in some case flows into spaces 21 in housing 20a of tray 20 so that when it hardens it locks into tray 20. The method 100 may include an additional step of performing the guided dental surgery while system 10, including tray 20 and lock 40, remain in place in a sturdy and stable position without regard to forces exerted on system 10.

Step 140 may involve unlocking the lock 40 or removing the locking wedge 40 and then removing the fixation tray 20, for example easily and rapidly with limited force without damaging the tooth or teeth. For example, the locking wedge 40 is removed in certain embodiments rapidly by exerting a force on it for example using an instrument that is operatively connected to the element in a cavity 62 of the fixation tray 20. Removing the fixation tray 20 may be accomplished in certain embodiments by exerting a force that generates stress such as shear stress on the housing 20a that may translate into stress such as shear stress on the crisp or brittle hardened material (formerly flowable or malleable material). In one non-limiting implementation, this may be accomplished by exerting a force (such as a rotational force) on an element (such as a pole 65) of tray 20. For example the force may be applied to an internal element of tray 20. In one implementation, the force may be applied to an element situated in a cavity 62 of the fixation tray 20 such as in top portion 26 of tray 20 (which in some embodiments is a cavity 62 in a holder 28 of top portion 26) to generate pressure causing stress such as shear stress on portions of the tray 20 and on the hardened material to break at least a portion of the hardened material (for example on an occlusal surface of the plurality of teeth), thereby allowing the sides or side portions of housing 20a (including arm extensions 32, 34 or including steps 23a, 23b) to flex and dislodge the fixation tray 20 from the plurality of teeth.

FIG. 1 is an exploded view that allows the visualization of the element in the cavity 62 according to one embodiment. A tracking device connector or handle 60 includes a pole portion 65 configured to fit inside cavity 62. In order to begin the process of removing the fixation tray 20, one can exert a rotational force on pole 65. This has the effect of pressuring the entire fixation tray 20 but in particular on the sides of tray 20, for example arm extensions 22, 24 of tray 20. It may have the effect of pressuring holder 28, top portion 26, side walls 22, 24 and arm extensions 32, 34. It may have an additional effect of exerting stress such as a shear stress and breaking at least a portion of the hardened material, for example on an occlusal surface of the plurality of teeth, thereby allowing side portions of housing 20a to flex so as to dislodge fixation tray 20 from the one or the plurality of teeth and remove fixation tray 20.

In method 100 (or method 200, 300, 400) if an element for example pole 65, has been placed in tray 20, then step 140 may also include removing a fastener or screw that locks pole 65.

Another method 200 shown in FIG. 17 may comprise a step 210 of deploying a fixation tray holding a flowable or malleable material over one or a plurality of teeth, the fixation tray having at a least a portion such as side walls configured to flex under stress, and a top portion connecting them and having extra flexible arm extensions inward-facing to urge the flowable or malleable material against the one or more teeth. For example, arm extensions 32, 34 may extend from a portion of side walls 22, 24 (or side portions of housing 20a) and in some cases from a free end, or from a point adjacent to a free end, of each of the side walls of the fixation tray 20, and the arm extensions 32, 34 may be inward-directed (and may be inclined) to urge the flowable or malleable material against the one or the plurality of teeth.

Step 220 of method 200 may comprise locking the fixation tray such as by deploying a locking wedge 40 over the fixation tray 20, for example to grip the fixation tray 20, for example to limit a movement of the side walls of the fixation tray. Step 230 may involve allowing the flowable or malleable material to harden into a rigid state that is crisp or brittle. The flowable or malleable material in some case flows into spaces 21 in housing 20a of tray 20 so that when it hardens it locks into the tray 20. Method 200 may include an additional step of performing the surgery while system 10, including tray 20 and lock 40, remain in place in a sturdy and stable position without regard to forces exerted on system 10.

Step 240 may comprise unlocking the lock or removing the locking wedge and then removing the fixation tray by exerting a force on an element of the fixation tray such as by rotating a pole or other element in a cavity of the fixation tray such as its top portion 26, thereby generating pressure against the housing 20a which causes at least portions of the housing 20a to flex (the portions may be sides that include arm extensions 32, 34) and which may causes breakage of the material, which allows dislodging the fixation tray from the plurality of teeth.

A flow chart of another method 300 is shown in FIG. 18. It includes a step 310 of deploying a fixation tray holding a flowable or malleable material over one or a plurality of teeth, the fixation tray having somewhat side walls configured to urge the flowable or malleable material against the tooth or teeth for example using any mechanism described above with respect to system 10 including for example either extra flexible inwardly facing arm extensions 32, 34 or using inwardly facing steps 23a, 23b. Locking the fixation tray using a lock on the tray or by deploying a locking wedge over the fixation tray may comprise a step 320 of method 300. Allowing the flowable or malleable material to harden is step 330. The flowable or malleable material in some case flows into spaces 21 in housing 20a of tray 20 so that when it hardens it locks into the tray 20. Method 300 may include an additional step of performing the surgery while system 10, including tray 20 and lock 40, remain in place in a sturdy and stable position without regard to forces exerted on system 10. Step 340 may comprise unlocking the lock such as by removing the locking wedge and then removing the fixation tray by exerting a force on an element in a cavity of the fixation tray so as to break the hardened material.

Method 400 may comprise a step 410 of deploying a fixation tray holding a flowable or malleable material over one or more teeth, the fixation tray 20 having a housing 20*a* defining a chamber 25 and having a mechanism to urge the material against the one or more teeth. Step 420 may comprise locking the fixation tray 20 to reduce or eliminate its freedom of movement. Step 430 may comprise allowing the material to harden and performing the guided surgery while the tray 20 and lock 40 remain in place in a sturdy and stable position. Step 440 may comprise removing or unlocking the lock 40 and then removing the fixation tray 20. Any suitable version of any of the elements described herein for system 10 may be used for that element in method 400.

By using a tray 20 in any of methods 100, 200, 300, 400 or system 10 having at least a portion configured to flex under stress, the system 10 is designed to break the hardened material when pressure is exerted for example by rotating an element such as pole 65 in cavity 62 of top portion 26 of tray 20. As a result of the tray 20 having a portion or portions configured to flex under stress exerted on the fixation tray 20 results in pressure being exerted against the hardened (previously flowable or malleable) material. This breaks the hardened material and this hardened material comes off the teeth when the fixation tray 20 is dislodged. If the tray 20 were rigid it may simply take out the whole tooth or teeth. Since for stability reasons, system 10 fills an undercut of the plurality of teeth, there is no option to realistically just pull system straight up vertically.

As noted, connector 60 can be connected to or can itself be a registration body used in mating the CT coordinates and the real world coordinates for the guided dental surgery. Accordingly, in an embodiment of the invention, method 500 of registration includes a step of performing a computed tomography (CT) scan of the patient's teeth without the system 10 being attached to the teeth. Step 520 comprises deploying any version of system 10 over one or a plurality of teeth (including tray 20 holding flowable or malleable material and including lock 40) so that system 10 is firmly attached to the one or a plurality of teeth and such that a connector 60 is also rigidly attached to system 10 such as by rigid attachment to tray 20 of system 10 (connector 60 is typically outside or mostly outside the patient's mouth). Step 530 involves performing registration by taking a tracking device (used in conjunction with the guided dental surgery) and touching it along the one or plurality of teeth.

In another embodiment of the invention, method 600 of registration includes a step 610 of deploying any version of system 10 over one or a plurality of teeth (including tray 20 holding flowable or malleable material and including lock 40) so that system 10 is firmly attached to the one or a plurality of teeth and doing so such that connector 60 is also rigidly attached to system 10 such as by rigid attachment to tray 20 of system 10 (connector 60 is typically outside or mostly outside the patient's mouth). Step 620 comprises performing a computed tomography (CT) scan of the one or the plurality of the patient's teeth after deployment of the tray 20 and lock 40 and connector 60. Step 630 comprises performing registration by taking the tracking device (used in conjunction with the guided dental surgery) and either (i) touching it along points of the connector 60 to register the connector 60 or (ii) simply rigidly attaching it (the tracking device) to the connector 60 to register the connector 60 since the dental surgery navigation system's software deduces the coordinates of the connector 60 from the coordinates of the tracking device to which it is rigidly attached.

These two versions of the registration process (500, 600) can also be combined with any or all of the steps of methods 100, 200, 300, 400. As such, the step of removing the lock and tray (and/or allowing the material to harden) can be omitted from the list of steps of the registration method in some versions.

In one embodiment of the invention, a stable affixation system for guided dental implantation, comprises a fixation tray 20 having a housing 20*a* that defines a chamber 25 configured to house a flowable or malleable material and be placed over one or a plurality of teeth of a person during guided dental implantation surgery, the flowable or malleable material configured to harden into a crisp or brittle material so as to conform to a contour of the one or the plurality of teeth, the housing having a mechanism configured to urge the flowable or malleable material (and/or when it is already hardened) toward the one or the plurality of teeth. The system 10 also comprises a lock 40 or locking wedge 40 configured to lock tray 20 or be positioned on or over the fixation tray 20 so as to reduce or eliminate a freedom of movement of housing 20*a*. Housing 20*a* may include a mechanism configured to join the flowable or malleable material, once hardened, to housing 20*a* such that a greater separation force is required to separate the flowable or malleable material, once hardened, from the housing, than a separation force required to separate the flowable or malleable material from the one or the plurality of teeth.

The housing 20*a* may include a portion configured to flex upon stress. For example, housing 20*a* may have one or more recesses (as described above) and in some versions, locking wedge may include one or more corresponding projecting members. In some versions, locking wedge 40 includes a first locking wedge side wall 42 thicker than a first side wall 22 of housing 20*a* and a second locking wedge side wall 44 thicker than a second side wall 24 of housing 20*a*.

Housing may have sides at least a portion of which are configured to flex under stress. For example, sides 22, 24 may flex outwardly under stress. For example, free ends of sides 22, 24 may spread outwardly under stress. In some case, the further a portion of sides 22, 24 is from a top portion 26 of housing 20*a*, the more that portion of the sides spreads outwardly under stress (for example due to a clamping or holding force at or near the top portion 26 of housing 20*a*).

In some embodiments, housing 20*a* has a mechanism configured to hold at least part of a tracking element and a mechanism configured to exert a force or a stress such as shear stress on the housing and/or on the crisp or brittle material so as to break at least a portion of the crisp or brittle material and dislodge the fixation tray from the one or the plurality of teeth. When the force is applied, the portion or portions of housing 20*a* configured to flex may then flex making it easier to cause stress on the hardened material and easily dislodge tray 20.

For example, the force may be applied from inside of tray 20. In one implementation, housing 20*a* has a cavity 62 configured to receive a tracking element or a handle of a tracking element. Cavity 62 may also be configured to receive an element (such as a pole 65 of a connector 60 of the tracking device) configured to exert a force or stress such as shear stress on the housing 20*a* (or a portion of housing 20a or on side walls of housing 20a) and/or on the hardened material so as to break at least a portion of brittle material and thereby dislodge the fixation tray 20 from the one or the plurality of teeth.

The mechanism for customizing the system 10 to the individual patient's teeth in order to facilitate rapid placement of the system 10 may be implemented, as seen in FIG. 15, in certain embodiments, by customizing the housing to the individual patient's teeth. This is implemented in some cases by the flowable or malleable material and by providing housing 20a of fixation tray 20 with a pair of inwardly directed arm extensions 22, 24 or inwardly directed steps 23a, 23b configured to urge the flowable or malleable material against the one or the plurality of teeth (including after such material hardens into a rigid state).

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A stable affixation system for guided dental implantation, comprising:
    a fixation tray customizable to the patient including a housing that defines a chamber configured to house a flowable or malleable material and be placed over a top, front and rear of one or a plurality of teeth of a person, the one or the plurality occupying a portion of the person's row of teeth, during the guided dental implantation surgery, the housing having sides, at least a portion of the sides are configured to flex under stress, the sides configured to urge the flowable or malleable material against the teeth; and
    a lock positioned on the fixation tray so as to reduce or eliminate a freedom of movement of the fixation tray, wherein each of the side walls of the housing has a free end configured to fit closer to a gumline of each jaw of the person than an opposite end, wherein in at least one position of the system the free ends are configured to flex outward when subjected to a squeezing force at the opposite ends.

2. The affixation system of claim 1, wherein the fixation tray is configured to be placed over the plurality of teeth and wherein the chamber defined by the housing comprises a channel that is substantially straight along a direction of the row of teeth.

3. The affixation system of claim 1, wherein the lock has an inner surface configured to define a chamber into which at least a portion of the fixation tray is configured to fit either snugly or using a friction fit.

4. The affixation system of claim 1, wherein the lock includes a mechanism for fixating at least side portions of the housing rigidly in place.

5. The affixation system of claim 1, wherein the housing includes a structure configured to join the flowable or malleable material, once hardened, to the housing such that a greater separation force is required to separate the flowable or malleable material, once hardened, from the housing, than a separation force required to separate the flowable or malleable material from the one or the plurality of teeth.

6. The affixation system of claim 1, wherein the lock is configured to reduce a freedom of motion of each of a first side wall and of a second side wall of the fixation tray.

7. The affixation system of claim 1, wherein the housing comprises a pair of inclined, inwardly directed arm extensions that extend from an inner surface of the chamber.

8. The affixation system of claim 7, wherein the housing is made from a first material and the arm extensions are made of a second material that is flexible.

9. The affixation system of claim 1, wherein the lock has a first wall or projecting member configured to extend alongside one of the side walls of the housing and a second wall or projecting member configured to extend alongside a second of the side walls of the housing.

10. The affixation system of claim 1, wherein the fixation tray has recesses and the lock has corresponding projecting members.

11. The affixation system of claim 10, wherein the projecting members project from an inner surface of a top portion of the lock.

12. The affixation system of claim 10, wherein the recesses are substantially planar recesses situated such that when the projecting members mate with the substantially planar recesses, a first substantially planar projecting member adjacent to and inward of a first side wall of the fixation tray and a second substantially planar projecting member adjacent to and inward of a second side wall of the fixation tray.

13. The affixation system of claim 1, wherein the housing has an elongated cavity configured to receive a tracking element.

14. The affixation system of claim 1, wherein an end view of at least one of (i) the fixation tray or (ii) the lock is substantially U-shaped.

15. The affixation system of claim 1, wherein the housing includes arm extensions that are each configured to urge the flowable or malleable material to harden in an undercut of the one or the plurality of teeth to stabilize the system.

16. The affixation system of claim 1, wherein the fixation tray includes side walls and arm extensions and each of the arm extensions is more flexible than each of the side walls.

17. The affixation system of claim 1, wherein the housing has spaces configured to allow the flowable or malleable material to flow into and, once hardened, to lock into.

18. A stable affixation system for guided dental implantation, comprising:
    a fixation tray having a housing that defines a chamber configured to house a flowable or malleable material and be placed over a top, front and rear of one or a plurality of teeth of a person, the one or the plurality occupying a portion of the person's row of teeth, during the guided dental implantation surgery, the flowable or malleable material configured to harden into a crisp or brittle material so as to conform to a contour of the one or the plurality of teeth, the housing having a mechanism configured to urge the flowable or malleable material toward the one or the plurality of teeth; and
    a lock positioned over the fixation tray snugly or using a friction fit and so as to reduce or eliminate a freedom of movement of the fixation tray, the lock having a first lock side wall that extends alongside one of the side walls of the housing and a second lock side wall that extends alongside a second of the side walls of the housing,
    wherein each of the side walls of the housing has a free end configured to fit closer to a gumline of each jaw of the person than an opposite end, wherein in at least one position of the system the free ends are configured to flex outward when subjected to a squeezing force at the opposite ends.

19. The affixation system of claim 18, wherein the housing includes a mechanism configured to join the flowable or malleable material, once hardened, to the housing such that a greater separation force is required to separate the flowable or malleable material, once hardened, from the housing, than a separation force required to separate the flowable or malleable material from the one or the plurality of teeth.

20. The affixation system of claim 18, wherein the housing has a mechanism configured to hold at least part of a tracking element and a mechanism configured to exert stress on the housing and/or on the crisp or brittle material so as to break at least a portion of the crisp or brittle material and dislodge the fixation tray from the one or the plurality of teeth.

21. The affixation system of claim 18, wherein the fixation tray is configured to be placed over the plurality of teeth and wherein the chamber comprises a channel that is substantially straight in a direction along the row of teeth.

22. A stable affixation system for guided dental implantation, comprising:
   a fixation tray customizable to the patient including a housing that defines a chamber configured to house a flowable or malleable material and be placed over a top, front and rear of one or a plurality of teeth of a person, the one or the plurality occupying a portion of the person's row of teeth, during the guided dental implantation surgery, the housing having side walls, at least a portion of the side walls are configured to flex under stress, the side walls configured to urge the flowable or malleable material against the teeth,
   wherein the housing includes a locking mechanism configured to reduce or eliminate a freedom of movement of the fixation tray by reducing or eliminating an ability of the at least the portion of the sides of the housing to flex under stress,
   wherein each of the side walls of the housing has a free end configured to fit closer to a gumline of each jaw of the person than an opposite end, wherein in at least one position of the system the free ends are configured to flex outward when subjected to a squeezing force at the opposite ends.

23. The affixation system of claim 22, wherein the at least a portion of the sides of the housing are configured to flex such that the further that the at least a portion of the sides of the housing is situated from a top portion of the housing, the more the at least a portion of the sides of the housing is configured to spread outward under stress.

24. The affixation system of claim 22, further comprising a registration element configured to be rigidly attached to the tray.

* * * * *